US012683014B2

(12) United States Patent
Venkataraman et al.

(10) Patent No.: US 12,683,014 B2
(45) Date of Patent: \*Jul. 14, 2026

(54) MACHINE-LEARNING-ORIENTED SURGICAL VIDEO ANALYSIS SYSTEM

(71) Applicant: Verb Surgical Inc., Santa Clara, CA (US)

(72) Inventors: Jagadish Venkataraman, Menlo Park, CA (US); Pablo E. Garcia Kilroy, Menlo Park, CA (US)

(73) Assignee: Auris Health, Inc., Santa Clara, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/418,048

(22) Filed: Jan. 19, 2024

(65) Prior Publication Data

US 2024/0242818 A1     Jul. 18, 2024

Related U.S. Application Data

(63) Continuation of application No. 17/530,232, filed on Nov. 18, 2021, now Pat. No. 11,901,065, which is a
(Continued)

(51) Int. Cl.
*G16H 30/40* (2018.01)
*G06N 20/00* (2019.01)
(Continued)

(52) U.S. Cl.
CPC ............ *G16H 30/40* (2018.01); *G06N 20/00* (2019.01); *G06V 20/41* (2022.01); *G06V 20/44* (2022.01);
(Continued)

(58) Field of Classification Search
CPC ........ G16H 30/40; G16H 30/20; G06N 20/00; G06V 20/70; G06V 20/49; G06V 20/46; G06V 20/41; G06V 20/44; G06V 2201/03
(Continued)

(56) References Cited

U.S. PATENT DOCUMENTS

| | | | | |
|---|---|---|---|---|
| 5,740,801 A | * | 4/1998 | Branson .................... | G06T 7/20 600/407 |
| 6,920,347 B2 | * | 7/2005 | Simon .................... | A61B 90/36 600/407 |

(Continued)

FOREIGN PATENT DOCUMENTS

| | | |
|---|---|---|
| CN | 104000655 A | 8/2014 |
| CN | 105992996 A | 10/2016 |

(Continued)

OTHER PUBLICATIONS

Advisory Action received for U.S. Appl. No. 15/987,782, mailed on Nov. 10, 2020, 2 pages.
(Continued)

*Primary Examiner* — Michael Tomaszewski
(74) *Attorney, Agent, or Firm* — Aikin & Gallant, LLP

(57) ABSTRACT

Embodiments described herein provide various examples of a surgical video analysis system for segmenting surgical videos of a given surgical procedure into shorter video segments and labeling/tagging these video segments with multiple categories of machine learning descriptors. In one aspect, a process for processing surgical videos recorded during performed surgeries of a surgical procedure includes the steps of: receiving a diverse set of surgical videos associated with the surgical procedure; receiving a set of predefined phases for the surgical procedure and a set of machine learning descriptors identified for each predefined phase in the set of predefined phases; for each received surgical video, segmenting the surgical video into a set of
(Continued)

video segments based on the set of predefined phases and for each segment of the surgical video of a given predefined phase, annotating the video segment with a corresponding set of machine learning descriptors for the given predefined phase.

20 Claims, 6 Drawing Sheets

Related U.S. Application Data continuation of application No. 15/987,782, filed on May 23, 2018, now Pat. No. 11,205,508.

(51) Int. Cl.
| | | |
|---|---|---|
| *G06V 20/40* | (2022.01) | |
| *G06V 20/70* | (2022.01) | |
| *G16H 30/20* | (2018.01) | |

(52) U.S. Cl.
CPC .............. *G06V 20/46* (2022.01); *G06V 20/49* (2022.01); *G06V 20/70* (2022.01); *G16H 30/20* (2018.01); *G06V 2201/03* (2022.01)

(58) Field of Classification Search
USPC ........................................................ 705/2–3
See application file for complete search history.

(56) References Cited

U.S. PATENT DOCUMENTS

| | | | | |
|---|---|---|---|---|
| 7,068,842 | B2 * | 6/2006 | Liang .................... | A61B 5/1116 |
| | | | | 382/103 |
| 7,317,955 | B2 * | 1/2008 | McGreevy ............. | G16H 40/63 |
| | | | | 600/101 |
| 7,379,790 | B2 | 5/2008 | Toth et al. | |
| 7,840,042 | B2 * | 11/2010 | Kriveshko .......... | A61B 5/1077 |
| | | | | 348/66 |
| 7,853,305 | B2 | 12/2010 | Simon et al. | |
| 8,086,008 | B2 * | 12/2011 | Coste-Maniere ...... | A61B 34/10 |
| | | | | 382/128 |
| 8,108,072 | B2 * | 1/2012 | Zhao ...................... | A61B 34/37 |
| | | | | 700/250 |
| 8,131,031 | B2 * | 3/2012 | Lloyd ..................... | G16Z 99/00 |
| | | | | 382/128 |
| 8,147,503 | B2 * | 4/2012 | Zhao ...................... | A61B 34/37 |
| | | | | 382/128 |
| 8,443,279 | B1 * | 5/2013 | Hameed .............. | G06F 16/7867 |
| | | | | 715/201 |
| 8,504,136 | B1 * | 8/2013 | Sun ...................... | A61B 5/1076 |
| | | | | 600/407 |
| 8,527,094 | B2 * | 9/2013 | Kumar ................... | A61B 34/70 |
| | | | | 600/101 |
| 8,600,551 | B2 * | 12/2013 | Itkowitz ................. | A61B 34/77 |
| | | | | 700/250 |
| 8,706,184 | B2 * | 4/2014 | Mohr .............. | A61B 1/000094 |
| | | | | 600/407 |
| 9,025,247 | B1 | 5/2015 | Mossberg et al. | |
| 9,215,293 | B2 * | 12/2015 | Miller .................... | G06F 3/011 |
| 9,413,976 | B2 * | 8/2016 | DiCarlo .............. | A61B 90/361 |
| 10,169,535 | B2 * | 1/2019 | Mentis ................. | A61B 1/0005 |
| 10,433,914 | B2 * | 10/2019 | Wollowick ........... | G06T 7/0014 |
| 10,499,996 | B2 * | 12/2019 | de Almeida Barreto ..................... | |
| | | | | A61B 34/10 |
| 10,588,699 | B2 * | 3/2020 | Richmond ............. | A61B 34/37 |
| 10,679,743 | B2 * | 6/2020 | Venkataraman ....... | G06Q 10/08 |
| 10,740,552 | B2 * | 8/2020 | Hanning ............... | G16H 40/20 |
| 10,803,320 | B2 * | 10/2020 | Calmus .................. | G08B 25/10 |
| 11,081,229 | B2 * | 8/2021 | Alvi ...................... | G16H 30/20 |
| 11,176,945 | B2 * | 11/2021 | Paul ...................... | G06N 20/00 |
| 11,189,379 | B2 * | 11/2021 | Giataganas ............. | G06F 16/22 |
| 11,202,676 | B2 * | 12/2021 | Lightcap .............. | A61B 5/4836 |
| 11,205,508 | B2 * | 12/2021 | Venkataraman ....... | G16H 30/40 |

| | | | | |
|---|---|---|---|---|
| 2003/0208196 | A1 * | 11/2003 | Stone ..................... | A61B 18/14 |
| | | | | 606/41 |
| 2005/0251156 | A1 * | 11/2005 | Toth ....................... | G16H 40/40 |
| | | | | 606/153 |
| 2008/0003555 | A1 | 1/2008 | Ekvall et al. | |
| 2010/0285438 | A1 * | 11/2010 | Kesavadas ........... | G09B 23/285 |
| | | | | 434/262 |
| 2011/0301447 | A1 * | 12/2011 | Park ...................... | G06T 7/0016 |
| | | | | 600/407 |
| 2012/0046659 | A1 | 2/2012 | Mueller | |
| 2012/0253360 | A1 * | 10/2012 | White .................... | A61B 34/35 |
| | | | | 606/130 |
| 2013/0211588 | A1 | 8/2013 | Diolaiti | |
| 2014/0286533 | A1 * | 9/2014 | Luo ........................ | G06V 40/18 |
| | | | | 382/103 |
| 2015/0005622 | A1 * | 1/2015 | Zhao ...................... | G16H 40/67 |
| | | | | 382/103 |
| 2015/0230875 | A1 * | 8/2015 | Shademan ........... | A61B 5/7425 |
| | | | | 600/407 |
| 2016/0100909 | A1 * | 4/2016 | Wollowick ............. | A61B 6/505 |
| | | | | 600/424 |
| 2016/0103810 | A1 * | 4/2016 | Hanning ................ | G16H 30/40 |
| | | | | 715/226 |
| 2016/0140875 | A1 | 5/2016 | Kumar et al. | |
| 2016/0166345 | A1 | 6/2016 | Kumar et al. | |
| 2016/0210411 | A1 * | 7/2016 | Mentis .................. | G06F 3/0304 |
| 2017/0035517 | A1 | 2/2017 | Geri et al. | |
| 2017/0132785 | A1 * | 5/2017 | Wshah .................. | G06T 7/0012 |
| 2018/0174311 | A1 | 6/2018 | Kluckner et al. | |
| 2018/0357514 | A1 * | 12/2018 | Zisimopoulos .......... | G06N 3/08 |
| 2019/0069957 | A1 * | 3/2019 | Barral ..................... | A61B 34/30 |
| 2019/0362834 | A1 * | 11/2019 | Venkataraman ....... | G16H 30/40 |
| 2021/0000461 | A1 * | 1/2021 | Charles .................. | A61B 90/37 |
| 2021/0290317 | A1 * | 9/2021 | Sen ........................ | A61B 34/20 |
| 2024/0242818 | A1 * | 7/2024 | Venkataraman ....... | G16H 30/40 |
| 2025/0062020 | A1 * | 2/2025 | Gordon .................. | G16H 50/20 |

FOREIGN PATENT DOCUMENTS

| | | |
|---|---|---|
| CN | 107667380 A | 2/2018 |
| EP | 2420197 A2 | 2/2012 |
| KR | 10-2008-0001622 A | 1/2008 |
| KR | 10-2014-0126322 A | 10/2014 |
| WO | 2016/200887 A1 | 12/2016 |
| WO | 2017/075541 A1 | 5/2017 |

OTHER PUBLICATIONS

Extended European Search Report for European Application No. 18920011.6 mailed Feb. 3, 2022, 10 pages.

Extended European Search Report for European Application No. 18933279.4 mailed May 17, 2022, 9 pages.

Final Office Action received for U.S. Appl. No. 15/987,782, mailed on Aug. 17, 2020, 24 pages.

International Preliminary Report on Patentability for International Application No. PCT/US2018/036452 mailed Dec. 3, 2020, 7 pages.

International Search Report and Written Opinion for International Application No. PCT/US2018/036452 mailed Aug. 31, 2018, 8 pages.

Lin, Henry C., et al., "Towards automatic skill evaluation: Detection and segmentation of robot-assisted surgical motions," Computer Aided Surgery, vol. 11, No. 5, Dec. 31, 2006, pp. 220-230.

Loukas, C. Video content analysis of surgical procedures. Surg Endosc 32, 553-568 (2018). https://doi.org/10.1007/s00464-017-5878-1. Received: Feb. 14, 2017 /Accepted: Sep. 7, 2017 / Published online: Oct. 26, 2017 © Springer Science+Business Media, LLC 2017 (Year: 2017).

Non-Final Office Action received for U.S. Appl. No. 15/987,782, mailed on Feb. 5, 2021, 30 pages.

Non-Final Office Action received for U.S. Appl. No. 15/987,782, mailed on Jan. 24, 2020, 20 pages.

Non-Final Office Action received for U.S. Appl. No. 17/530,232, mailed on Feb. 17, 2023, 20 pages.

(56)     References Cited

OTHER PUBLICATIONS

Notice of Allowance for U.S. Appl. No. 16/894,018 mailed Sep. 29, 2022, 10 pages.
Notice of Allowance received for U.S. Appl. No. 15/987,782, mailed on Aug. 18, 2021, 11 pages.
Notification of Reasons for Refusal for Japanese Application No. 2020-562174 mailed Jan. 18, 2022, 6 pages.
Office Action received for Chinese Patent Application No. 201880001594.4, mailed on Feb. 1, 2024, 24 pages (14 pages of English Translation and 10 pages of Original Document).
Office Action received for European Application No. 18920011.6, mailed on Jan. 24, 2024, 5 pages.
Padoy, Nicolas, "Workflow and Activity Modeling for Monitoring Surgical Procedures," HAL archvies-ouvertes.fr, retrieved from the Internet <http://www.theses.fr/2010NAN10025/document, Apr. 14, 2010, 166 pages.
European Search Report received for European Patent Application No. 25205240.2, mailed Dec. 10, 2025, 8 pages.

* cited by examiner

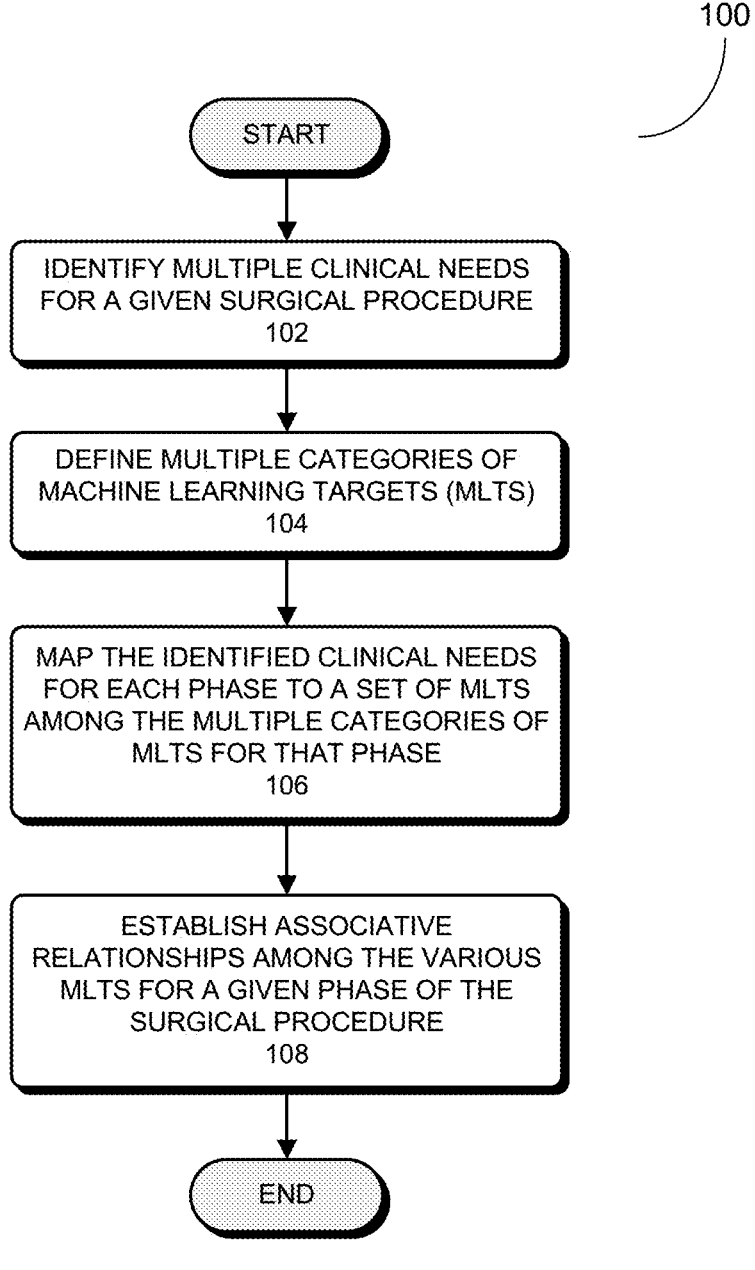

100

START

IDENTIFY MULTIPLE CLINICAL NEEDS
FOR A GIVEN SURGICAL PROCEDURE
102

DEFINE MULTIPLE CATEGORIES OF
MACHINE LEARNING TARGETS (MLTS)
104

MAP THE IDENTIFIED CLINICAL NEEDS
FOR EACH PHASE TO A SET OF MLTS
AMONG THE MULTIPLE CATEGORIES OF
MLTS FOR THAT PHASE
106

ESTABLISH ASSOCIATIVE
RELATIONSHIPS AMONG THE VARIOUS
MLTS FOR A GIVEN PHASE OF THE
SURGICAL PROCEDURE
108

END

FIG. 1

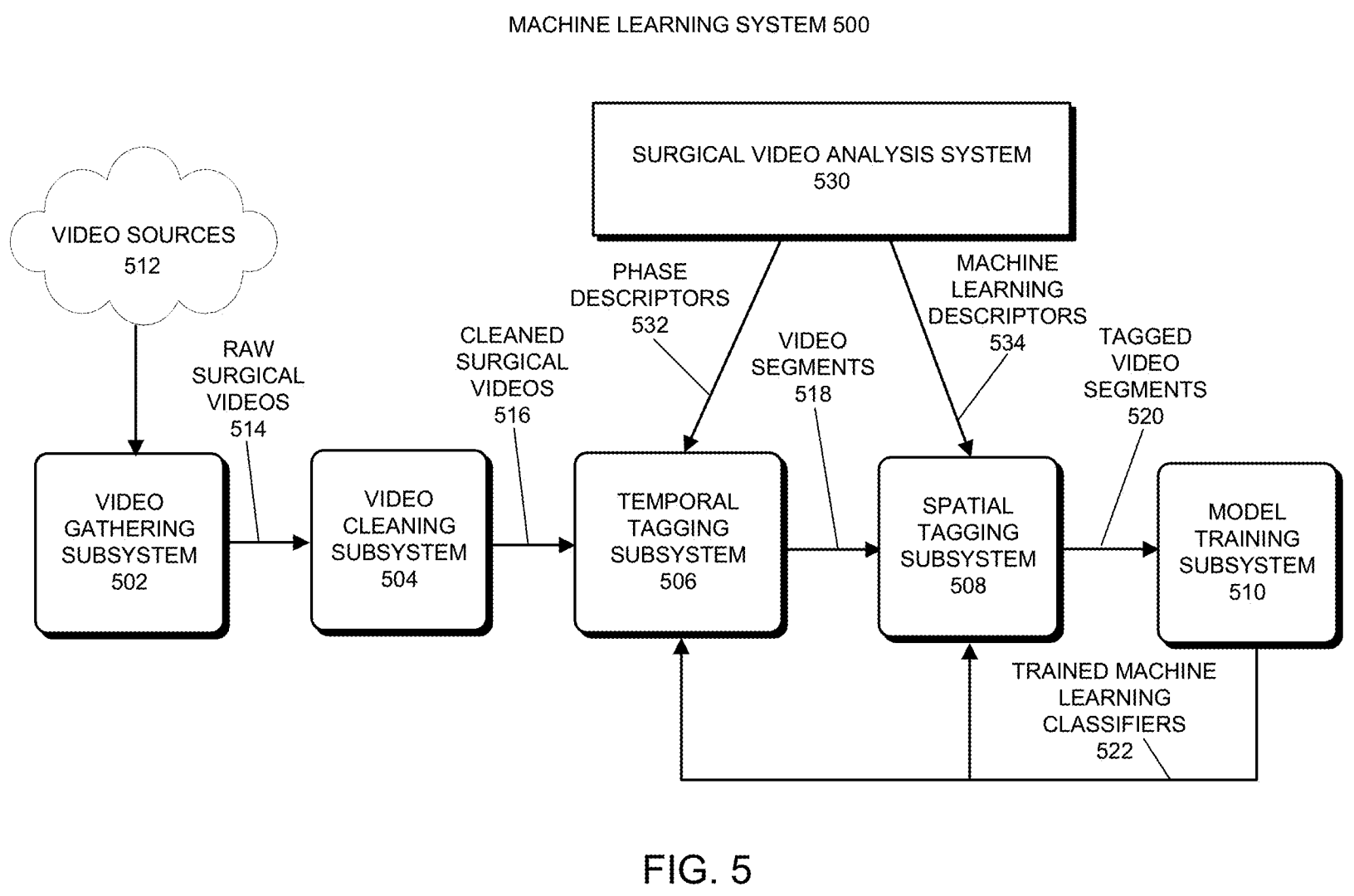

MACHINE LEARNING SYSTEM 500

SURGICAL VIDEO ANALYSIS SYSTEM 530

MODEL TRAINING SUBSYSTEM 510

TAGGED VIDEO SEGMENTS 520

MACHINE LEARNING DESCRIPTORS 534

SPATIAL TAGGING SUBSYSTEM 508

TRAINED MACHINE LEARNING CLASSIFIERS 522

VIDEO SEGMENTS 518

PHASE DESCRIPTORS 532

TEMPORAL TAGGING SUBSYSTEM 506

CLEANED SURGICAL VIDEOS 516

VIDEO CLEANING SUBSYSTEM 504

RAW SURGICAL VIDEOS 514

VIDEO SOURCES 512

VIDEO GATHERING SUBSYSTEM 502

FIG. 5

MACHINE-LEARNING-ORIENTED SURGICAL VIDEO ANALYSIS SYSTEM

CROSS-REFERENCE TO RELATED APPLICATIONS

This application is a continuation of U.S. patent application Ser. No. 17/530,232, filed Nov. 18, 2021, which is a continuation of U.S. patent application Ser. No. 15/987,782, filed May 23, 2018, now U.S. Pat. No. 11,205,508, issued Dec. 21, 2021, which are hereby incorporated by reference in their entirety.

TECHNICAL FIELD

The present disclosure generally relates to building surgical video analysis tools, and more specifically to systems, devices and techniques for segmenting surgical case videos of a surgical procedure into key phases and mining machine learning-oriented surgical data from the video segments to facilitate improving outcomes of surgeries and skills of surgeons.

BACKGROUND

Recorded videos of medical procedures such as surgeries contain highly valuable and rich information for medical education and training, assessing and analyzing the quality of the surgeries and skills of the surgeons, and for improving the outcomes of the surgeries and skills of the surgeons. There are many surgical procedures which involve displaying and capturing video images of the surgical procedures. For example, almost all minimally invasive procedures (MIS), such as endoscopy, laparoscopy, and arthroscopy, involve using video cameras and video images to assist the surgeons. Furthermore, the state-of-the-art robotic-assisted surgeries require intraoperative video images being captured and displayed on the monitors for the surgeons. Consequently, for many of the aforementioned surgical procedures, e.g., a gastric sleeve or cholecystectomy, a large cache of surgical videos already exist and continue to be created as a result of a large number of surgical cases performed by many different surgeons from different hospitals.

The simple fact of the existence of a huge (and constantly increasing) number of surgical videos of a particular surgical procedure makes processing and analyzing the surgical videos of the given procedure a potential machine learning problem. However, there is no known existing effort for mining these surgical videos to build machine learning models for the purposes of evaluating and improving the outcomes of the surgical procedures and skills of the surgeons.

SUMMARY

In this patent disclosure, various examples of a surgical video analysis system for breaking down a given surgical procedure into key phases, identifying clinical needs in each of the phases, translating these clinical needs into machine learning targets, and eventually integrating these machine learning targets into various product features for the customers are disclosed. In various embodiments, the disclosed surgical video analysis system can identify various machine learning targets from each phase of a given surgical procedure to satisfy the identified clinical needs associated with each phase of the surgical procedure. The disclosed surgical video analysis system can also establish associative relationships among these machine learning targets to identify and output classifiers for machine learning.

In various embodiments, the disclosed surgical video analysis system further uses the established phases to break down surgical videos of the given surgical procedure into shorter video segments and uses the identified machine learning targets to label/tag these video segments into different categories of descriptors including surgical phases, surgical sub-phases or tasks, surgical tools, anatomies, complications, and tips and tricks. Moreover, for each phase, the disclosed surgical video analysis system can establish associative relationships among the different categories of descriptors for the given phase by creating a set of metrics based on the different categories of descriptors, wherein the set of metrics can be used to evaluate the skills of the surgeon and the quality of the surgery. After segmenting and labeling/tagging surgical videos with different categories of descriptors for a given surgical procedure, the disclosed video analysis system can create independent databases for each of these descriptors for video content retrieval. In addition to analyzing and archiving surgical videos, the general concepts of the disclosed video analysis system can be used to analyze and mine data, features, and events from videos in other technological domains and build independent databases for the mined data, features, and events.

In one aspect, a process for processing robotic surgical videos of a surgical procedure performed using a surgical robot is disclosed. This process can begin by receiving a diverse set of surgical videos associated with the surgical procedure. The process additionally receives a set of predefined phases for the surgical procedure and a set of machine learning descriptors identified for each predefined phase in the set of predefined phases. Next, for each received surgical video, the process segments the surgical video into a set of video segments based on the set of predefined phases. For each segment of the surgical video of a given predefined phase, the process annotates the video segment with a corresponding set of machine learning descriptors for the given predefined phase. Finally, the process stores the annotated surgical videos of the surgical procedure into a set of searchable databases.

In some embodiments, the set of surgical videos are gathered from a diverse group of doctors and hospitals who perform and record the surgical procedure.

In some embodiments, the process segments the surgical video into the set of video segments by detecting a phase boundary which separates two consecutive phases in the set of predefined phases.

In some embodiments, the process detects the phase boundary by detecting an initial appearance of a surgical tool as an indicator of the beginning of a given phase.

In some embodiments, the process detects the phase boundary by detecting the phase boundary includes detecting a given event in a set of events as an indicator of the beginning of a given phase. The set of events can include: a cautery event; a bleeding event; and an adhesion event.

In some embodiments, the process further includes the steps of: determining a severity value for the detected event; and assessing the skill of a surgeon performing the surgery based on the determined severity value.

In some embodiments, the process annotates the video segment with the corresponding set of machine learning descriptors by tagging objects in the video images of the video segment that match one or more of the corresponding set of machine learning descriptors with the matched machine learning descriptors.

In some embodiments, the process stores the annotated surgical videos of the surgical procedure by creating a separate database for a set of annotated video segments belonging to the same phase in the set of predefined phases.

In another aspect, a system for processing robotic surgical videos of a surgical procedure performed using a surgical robot is disclosed. This system includes: one or more processors; a memory coupled to the one or more processors; a receiving module for receiving a diverse set of surgical videos associated with the surgical procedure, a set of predefined phases for the surgical procedure, and a set of machine learning descriptors identified for each predefined phase in the set of predefined phases; a video segmentation module for segmenting each received surgical video into a set of video segments based on the set of predefined phases; a video annotation module for annotating each segment of a surgical video of a given predefined phase with a corresponding set of machine learning descriptors for the given predefined phase; and a database generation module for storing the annotated surgical videos of the surgical procedure into a set of searchable databases.

In yet another aspect, a process for identifying machine learning targets in robotic surgical videos for a given type of surgical procedure is disclosed. This process can first define a set of phases for the surgical procedure, wherein each phase in the set of phases represents a particular intraoperative stage of the surgical procedure. Next, for each phase in the set of phases, the process identifies a set of clinical needs and subsequently maps the set of clinical needs to a set of machine learning targets for the given phase. The process then aggregates the sets of machine learning targets to generate a collective set of machine learning targets for the surgical procedure.

In some embodiments, the process further identifies a set of subphases within a given phase in the set of phases, wherein each subphase corresponds to single task among a set of tasks which is required to complete the given phase of the surgical procedure.

In some embodiments, the set of clinical needs for the phase includes one or more of the following: warning potential or ongoing complications; recommending when to convert from an minimally invasive (MIS) procedure to an open procedure; providing reminder of surgical steps or checklists applicable to the given phase; highlighting critical and/or sensitive anatomy; displaying landmarks dissection planes and/or critical views; highlighting risks based on similar surgical steps; and assisting with intraoperative report or documentation.

In some embodiments, the process maps the set of clinical needs to the set of machine learning targets for the given phase by: receiving multiple categories of machine learning targets, wherein each category of machine learning targets comprises a set of surgical items of a similar nature; and for each category of machine learning targets, identifying a subset of machine learning targets in the category of machine learning targets that satisfies the set of clinical needs.

In some embodiments, the multiple categories of machine learning targets include one or more of: a set of surgical tools; a set of anatomies; a set of surgical tasks/events; a set of complications; and a set of tips and tricks.

In some embodiments, the process also includes the step of establishing a set of associative relationships among the set of machine learning targets for the given phase of the surgical procedure.

BRIEF DESCRIPTION OF THE DRAWINGS

The structure and operation of the present disclosure will be understood from a review of the following detailed description and the accompanying drawings in which like reference numerals refer to like parts and in which:

FIG. 1 presents a flowchart illustrating an exemplary process for establishing machine learning targets in preparation for mining surgical data from surgical videos of a given surgical procedure in accordance with some embodiments described herein.

FIG. 5 shows a block diagram of an exemplary machine learning system for training machine learning classifiers for automatically tagging surgical videos in accordance with some embodiments described herein.

DETAILED DESCRIPTION

Figure 2:
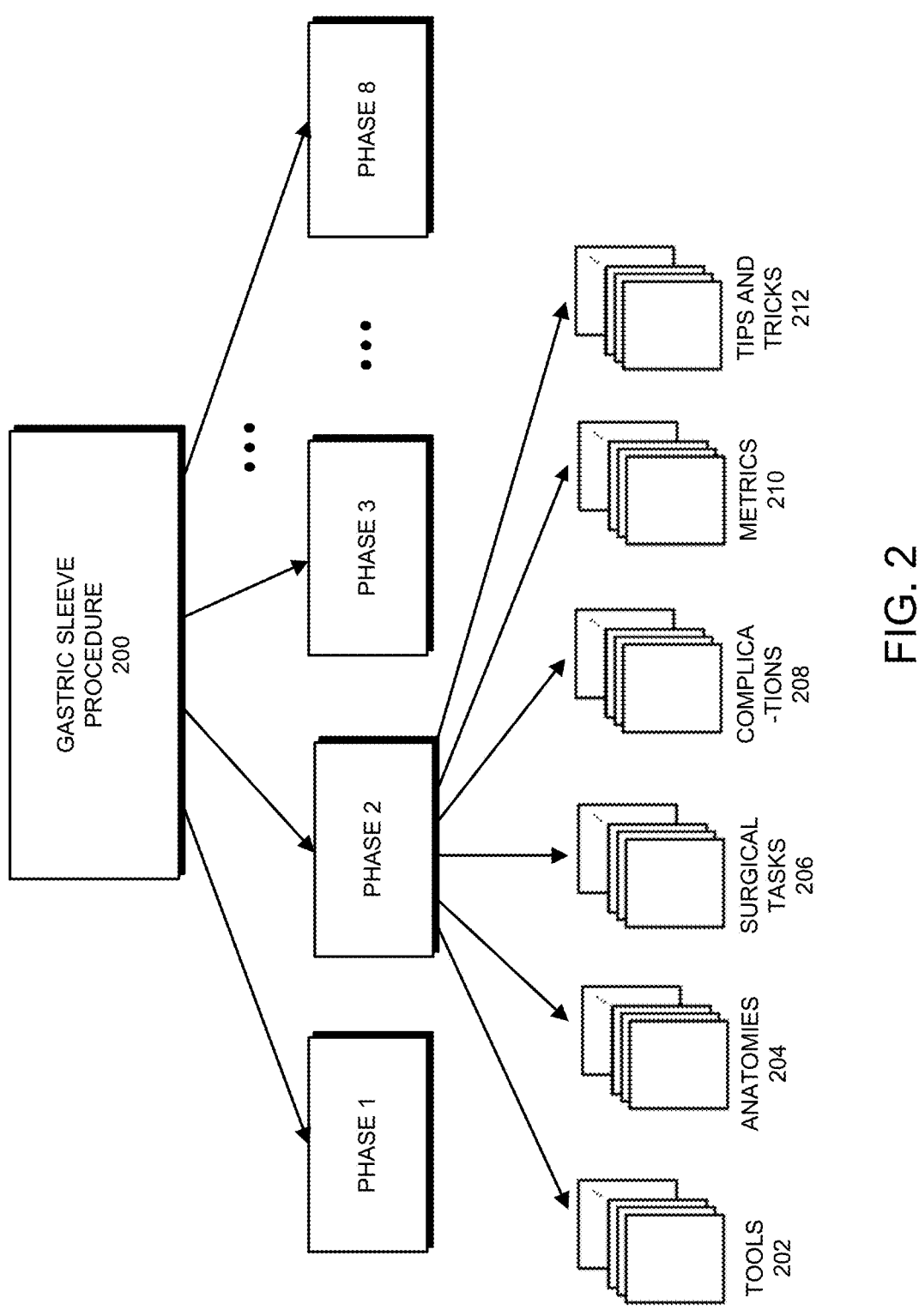
FIG. 2 shows a diagram illustrating an exemplary process for segmenting and identifying the sets of machine learning targets for the gastric sleeve procedure in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Recorded videos of medical procedures such as surgeries contain highly valuable and rich information for medical education and training, assessing and analyzing the quality of the surgeries and skills of the surgeons, and for improving the outcomes of the surgeries and skills of the surgeons. There are many surgical procedures which involve displaying and capturing video images of the surgical procedures. For example, almost all minimally invasive procedures (MIS), such as endoscopy, laparoscopy, and arthroscopy, involve using video cameras and video images to assist the surgeons. Furthermore, the state-of-the-art robotic-assisted surgeries require intraoperative video images being captured and displayed on the monitors for the surgeons. Consequently, for many of the aforementioned surgical procedures, e.g., a gastric sleeve or cholecystectomy, a large cache of surgical videos already exist and continue to be created as a result of a large number of surgical cases performed by many different surgeons from different hospitals. The simple fact of the existence of a huge (and constantly increasing) number of surgical videos of a particular surgical procedure makes processing and analyzing the surgical videos of the given procedure a potential machine learning problem. However, there is no known existing effort for mining these surgical videos to identify machine learning targets and to build machine learning models for the purposes of evaluating and improving the outcomes of the surgical procedures and skills of the surgeons.

One of the objectives of this patent disclosure is to provide a universal technique for breaking down surgical case videos (also referred to as "surgical videos," "surgical procedure videos," or "procedure videos" hereinafter) of any given surgical procedure into a set of manageable machine learning targets and subsequently establishing associative relationships among these machine learning targets to identify machine learning classifiers. To achieve this objective, the proposed surgical video analysis system is designed for breaking down a surgical video into predefined phases, identifying clinical needs in each of the phases, and translating these clinical needs into a set of machine learning targets. More specifically, the machine learning targets can be divided into different categories of descriptors including but not limited to, surgical phases, surgical subphases or tasks, surgical tools, anatomies, complications, and tips and tricks. While the disclosed systems and techniques are generally described with the help of a few specific surgical procedures, such as gastric bypass, sleeve gastrectomy, and cholecystectomy, the present disclosure is not meant to be limited to the above procedures. In general, the disclosed systems and techniques are applicable to any surgical procedure for which the surgery process can be recorded.

In this patent disclosure, various examples of a surgical video analysis system for breaking down a given surgical procedure into key phases, identifying clinical needs in each of the phases, translating these clinical needs into machine learning targets, and eventually integrating these machine learning targets into various product features for the customers are disclosed. In various embodiments, the disclosed surgical video analysis system can identify various machine learning targets from each phase of a given surgical procedure to satisfy the identified clinical needs associated with each phase of the surgical procedure. The disclosed surgical video analysis system can also establish associative relationships among these machine learning targets to identify and output classifiers for machine learning.

In various embodiments, the disclosed surgical video analysis system additionally uses the established phases to break down surgical videos of the given surgical procedure into shorter video segments and uses the identified machine learning targets to label/tag these video segments into different categories of descriptors including surgical phases, surgical sub-phases or tasks, surgical tools, anatomies, complications, and tips and tricks. Moreover, for each phase, the disclosed surgical video analysis system can establish associative relationships among the different categories of descriptors for the given phase by creating a set of metrics based on the different categories of descriptors, wherein the set of metrics can be used to evaluate the skills of the surgeon and the quality of the surgery. After segmenting and labeling/tagging surgical videos with different categories of descriptors for a given surgical procedure, the disclosed video analysis system can create independent databases for each of these descriptors for video content retrieval. In addition to analyzing and archiving surgical videos, the general concepts of the disclosed video analysis system can be used to analyze and mine data, features, and events from videos in other technological domains and build independent databases for the mined data, features, and events.

FIG. 1 presents a flowchart illustrating an exemplary process 100 for establishing machine learning targets in preparation for mining surgical data from surgical videos of a given surgical procedure in accordance with some embodiments described herein. In one or more embodiments, one or more of the steps in FIG. 1 may be omitted, repeated, and/or performed in a different order. Accordingly, the specific arrangement of steps shown in FIG. 1 should not be construed as limiting the scope of the technique.

Process 100 first identifies multiple clinical needs for the given surgical procedure (step 102). In some embodiments, one of the clinical needs includes segmenting a surgical video of the surgical procedure into a set of phases. In some embodiments, to meet the clinical need of segmenting a surgical video into a set of phases, the process first defines a set of phases for the surgical procedure. In some embodiments, each phase in the set of predefined phases represents a particular stage of the surgical procedure that serves a unique and distinguishable purpose in the entire surgical procedure. In some embodiments, a given surgical video described herein is recorded specifically for the intraoperative period of the surgical procedure. The predefined set of phases can be initially established based on a well-recognized and/or standardized operation procedure retrievable from a surgical information management system (IMS) which identifies key phases within a given surgical procedure. As described further below, the set of predefined phases can be used to partition the intraoperative surgical video, which can be a rather long video, into a set of shorter video segments, and each video segment corresponds to a particular stage of the surgical procedure which is distinguishable from other video segments corresponding to other stages of the surgical procedure.

Note that segmenting the given surgical procedure into the set predefined phases allows for analyzing the given surgical procedure one phase/stage at a time while equipped with an accurate understanding of the functions and operations involved in a given phase. In some embodiments, a given predefined phase can be further broken down into a set of subphases, wherein each subphase corresponds to single task among a set of tasks which are performed within the given predefined phase. In such embodiments, it is possible to further divide a phase segment of the surgical video into even smaller segments correspondent to the individual tasks associated with the given phase.

Using the gastric sleeve surgery procedure (also referred to as "sleeve gastrectomy," "gastric sleeve procedure," or "sleeve procedure" hereinafter) as an example, an exemplary breakdown of the procedure can include the following key phases: (1) identification of pylorus; (2) greater curvature mobilization; (3) mobilization of fundus; (4) posterior gastric dissection; (5) positioning of bougie; (6) sleeve pouch creation; (7) leak test; and (8) extraction of gastric remnant. As mentioned above, some of the phases listed above can also include multiple tasks, and a given phase comprising multiple tasks is typically performed in an ordered set of steps to complete the multiple tasks. For example, the greater-curvature-mobilization phase of the gastric sleeve procedure can be further broken down into a number of subphases corresponding to the following tasks: (1) entry into lesser sac; (2) mobilization of antrum; and (3) mobilization of stomach. As another example, the mobilization-of-fundus phase of the sleeve procedure can be further broken down into a number of subphases corresponding to the following tasks: (1) mobilization of fundus; and (2) division of gastric vessels. As yet another example, the posterior-gastric-dissection phase can be further broken down into a number of subphases corresponding to the following tasks: (1) mobilization of gastric cardia; and (2) posterior gastric dissection.

Mathematically, the relationship between a given surgical procedure P and the set of M predefined phases can be expressed as $P=\{P_1, P_2, P_3, \ldots, P_M\}$, wherein each $P_i$ (i=1, . . . , M) is a given predefined phase.

After defining the set of phases for segmenting a surgical video, the process 100 then identifies a set of clinical needs for each of the predefined phases. Typically, the set of clinical needs for a given phase specifies a checklist of things which are required to properly perform tasks within the given phase of the surgical procedure. Using the above-described gastric sleeve procedure as an example, during the posterior-gastric-dissection phase of the procedure, and immediate after the gastric cutting task, the cutting tool (e.g., an electrocautery tool) remains extremely hot and an accidental touching of nearby organs can cause severe organ injuries. Hence, in the posterior-gastric-dissection phase, the set of clinical needs can then include "avoiding accidental touching from the hot tool." Using cholecystectomy procedure (i.e., gallbladder removal) as another example, the set of predefined phases can include a "clipping-the-cystic-duct phase" for separating the gallbladder. In this phase, without correctly identifying the location of the cystic duct, the operation runs the risks of accidentally cutting, burning, or injuring the common bile duct which is nearby the cystic duct. Hence, the set of clinical needs in the clipping the cystic duct phase can include "identifying the correct location of the cystic duct."

It can be understood that, for each predefined phase in the set of phases, a set of unique clinical needs can be generated which specifies a checklist of things which are required for properly performing tasks within the predefined phase, and for improving the outcomes of the surgery. As such, the clinical needs for a given phase of the surgical procedure can be specified by a group of professionals or key opinion leaders (KOLs) with the required levels of experience and knowledge in the given procedure, and possibly with the assistant from a relevant knowledge database. When generating clinical needs for a given surgical procedure, the KOLs can consider a comprehensive list of factors for each phase and each task in each phase, including but are not limited to: (1) warnings of potential or ongoing complications (e.g., bleedings, organ injures, duct injuries, leak risk); (2) recommendations of when to convert from an MIS procedure to an open procedure based on the severities of bleeding, adhesion, or other complications; (3) assistance with objective measurements; (4) reminding of surgical steps or checklists applicable to the given phase/task; (5) highlighting critical anatomy; (6) displaying landmarks for procedures such as dissection planes or critical views; (7) sensitive anatomy, e.g., ureter, nerves, and vessels; (8) highlighting risks based on similar clinical scenarios; (9) providing tools to allow coordination between surgeon and surgeon assistance; and (10) helps with intraoperative report or documentation.

Referring back to FIG. 1, after the clinical needs have been identified for each of the set of predefined phases, the process defines multiple categories of machine learning targets (MLTs) (step 104). One exemplary composition of MLTs can include the follow categories: (1) tools; (2) anatomies; (3) surgical tasks/events; (4) complications; (5) metrics; and (6) tips and tricks. In some embodiments, the set of predefined phases which are associated with the clinical need of segmenting a surgical video are also a category of machine learning targets (MLTs), i.e., the phase MLTs. Note that other embodiments of the MLT categories can have fewer or greater number of categories than the example above.

The process 100 next maps the identified clinical needs for each phase to a set of MLTs among the multiple categories of MLTs for that phase (step 106). Using the above-described gastric sleeve procedure example, the clinical needs of "avoiding accidental touching from the hot tool" identified for the posterior-gastric-dissection phase requires the proper positioning of the cautery tool. Hence, this clinical need can be mapped to particular surgical tools in the tools category. Using the above-described cholecystectomy procedure example, the clinical needs of "identifying the correct location of the cystic duct" can be translated into the anatomy of the gallbladder in the anatomies category. In some embodiments, step 106 also includes mapping the set of predefined phases associated with the clinical need of segmenting a surgical video into the set of phase MLTs.

Note that different from the clinical needs which are generally specified as a set of objectives/concerns/warnings, the MLTs can typically be directly viewed and analyzed within a given phase segment of a surgical video. Moreover, a set of MLTs for a given phase can be used to evaluate/ assess the quality of the phase of the surgery to determine if the associated clinical needs for the phase have been satisfied. In some embodiments, each category of the MLTs described above can further include subcategories. For example, the tool category can include the following subcategories: (1) tool detection; (2) tool identification; and (3) tool tracking. The tool detection MLT relates to detecting a surgical tool in the video images; the tool identification MLT relates to identifying a detected surgical tool as a particular surgical tool; and the tool tracking MLT relates to tracking an identified tool through a sequence of video images for the changing position of the identified tool. Hence, the above-described clinical needs of "avoiding accidental touching from the hot tool" can also be mapped to a tool tracking MLT.

After step 106, a given surgical procedure is broken down into a set of phases and each phase is specified by a set of MLTs. Using the gastric sleeve procedure as an example, applying process 100 on this procedure generates outputs that include multiple categories of MLTs for each of the predetermined phases. For example, the sleeve-pouch-creation phase can include an anatomy category comprising the following identified MLTs: pylorus, greater curvature, lesser curvature, angularis incisura, and antrum; the greater-curvature-mobilization phase can include a complication category comprising the following identified MLTs: bleeding; stapler stuck; organ injury; vascular injury, adhesion, division of gastric vessel bleeding, stapling across gastric tube, and instrument failure; the mobilization-of-fundus phase can include a tool category comprising the following MLTs: harmonic tools; RF tools, Caman tools, grasper, stapler including staple load choice, retractor, measuring tape, and clip applier.

In some embodiments, after identifying the sets of MLTs for the set of phases, process 100 further establishes associative relationships among the various MLTs for a given phase of the surgical procedure (step 108). These associative relationships specify how MLTs from different MLT categories of the same phase may be linked to one another. For example, a given task MLT and/or a given tool MLT of a given phase can be often linked to a particular complication MLT identified for that phase. As another example, a given metric MLT in the set of metrics MLTs of a given phase is often linked to at least one of the tool/anatomy/task MLT identified for that phase. In some embodiments, during a machine learning model training operation, these associative relationships among the various MLTs for a given phase can be used to describe the different output classes and the underlying sub-classes.

FIG. 2 shows a diagram illustrating an exemplary process of segmenting and identifying the sets of machine learning targets for the gastric sleeve procedure in accordance with some embodiments described herein. As can be seen in FIG. 2, gastric sleeve procedure 200 is broken down into eight phases, i.e., Phase 1: identification of pylorus; Phase 2: greater curvature mobilization; Phase 3: mobilization of fundus; Phase 4: posterior gastric dissection; Phase 5: positioning of bougie; Phase 6: sleeve pouch creation; Phase 7: leak test; and Phase 8: extraction of gastric remnant. FIG. 2 also shows that Phase 2 is associated with six categories of MLTs, i.e., tools 202; anatomies 204; surgical tasks 206; complications 208; metrics 210; and tips and tricks 212. Due to the constraint of the viewing area, the identified MLTs for other phases of gastric sleeve procedure 200 are not explicitly shown. However, an example composition of MLTs for Phases 1-6 of gastric sleeve procedure 200 is listed below.

Phase 1: Identification of Pylorus
    Anatomies MLTs:
        Pylorus;
    Metrics MLTs:
        Pylorus identified? (Y/N) (OM);
Phase 2: Greater Curvature Mobilization
    Tools MLTs:
        Harmonic;
        RF;
        Caman;
        grasper;
        stapler;
        retractor;
        measuring tape;
        clip applier;
    Anatomies MLTs:
        liver;
        left crus; and
        omentum;
    Surgical tasks MLTs:
        entry into lesser sac;
        mobilization of antrum; and
        mobilization of stomach;
    Complications MLTs:
        bleeding;
        stapler stuck;
        vascular injury;
        adhesion;
        organ injury;
        division of gastric vessel bleeding;
        stapling across gastric tube; and
        instrument failure;
    Metrics MLTs:
        bleeding encountered at splenic hilum (Y/N) (OM);
        pylorus identified? (Y/N) (OM); and
        clip applier used? (Y/N) (OM) (inferred);
    Tips and tricks MLTs:
        if too much adhesion→create pouch first.
Phase 3: Mobilization of Fundus
    Tools MLTs:
        Harmonic;
        RF;
        Caman;
        grasper;
        stapler,
        retractor;

measuring tape;
        clip applier;
    Anatomies MLTs:
        left crus;
    Surgical tasks MLTs:
        division of gastric vessel;
    Complications MLTs:
        bleeding;
        stapler stuck;
        vascular injury;
        adhesion;
        organ injury;
        division of gastric vessel bleeding;
        stapling across gastric tube; and
        instrument failure;
    Metrics MLTs:
        bleeding (Y/N) (inferred) (OM);
        clip applier used? (Y/N) (inferred) (OM); and
    Left crus adequately visualized? (Y/N) (SM);
Phase 4: Posterior Gastric Dissection
    Surgical tasks MLTs:
        mobilization of gastric cardia;
    Metrics MLTs:
        posterior gastric dissection adequate (Y/N) (SM);
Phase 5: Positioning of Bougie
    Tools MLTs:
        Harmonic;
        RF;
        Caman;
        grasper;
        stapler;
        retractor;
        measuring tape;
        clip applier;
    Anatomies MLTs:
        pylorus in view; and
        stomach in view;
    Complications MLTs:
        bleeding;
        stapler stuck;
        vascular injury;
        adhesion;
        organ injury;
        division of gastric vessel bleeding;
        stapling across gastric tube; and
        instrument failure;
    Metrics MLTs:
        bougie diameter measured (Y/N) (inferred) (OM);
        bleeding? (Y/N) (inferred) (OM); and
        clip applier used? (Y/N) (inferred) (OM);
Phase 6: Sleeve Pouch Creation
    Tools MLTs:
        Harmonic;
        RF;
        Caman;
        grasper;
        stapler;
        retractor;
        measuring tape;
        clip applier;
    Anatomies MLTs:
        pylorus;
        greater curvature;
        lesser curvature; and
        antrum;
    Complications MLTs:
        bleeding;
        stapler stuck;

vascular injury;
adhesion;
organ injury;
division of gastric vessel bleeding;
stapling across gastric tube; and
instrument failure;
Metrics MLTs:
seamguard used? (Y/N) (OM);
tissue/fibrin sealant used? (Y/N) (OM);
oversew staple line? (Y/N) (OM);
number of staple fires (OM);
distance from Pylorus (OM);
size of bougie (OM);
distance to angularis incisura (OM);
distance to GE junction (OM);
last staple line—can the stapler be clearly seen (OM);
staple line—spiral (Y/N) (OM);
staple line—bleeding (Y/N) (OM);
staple line—malformation (Y/N) (OM).

Note that for the metrics category of MLTs, the MLTs can be divided into objective metrics (OMs) and subjective metrics (SMs). For example, in Phase 3—mobilization of fundus, the first two metrics MLTs are OMs and the last MLT is an SM. Note also that in the exemplary list of MLTs above, Phases 7-8 do not have associated MLTs.

Figure 3:
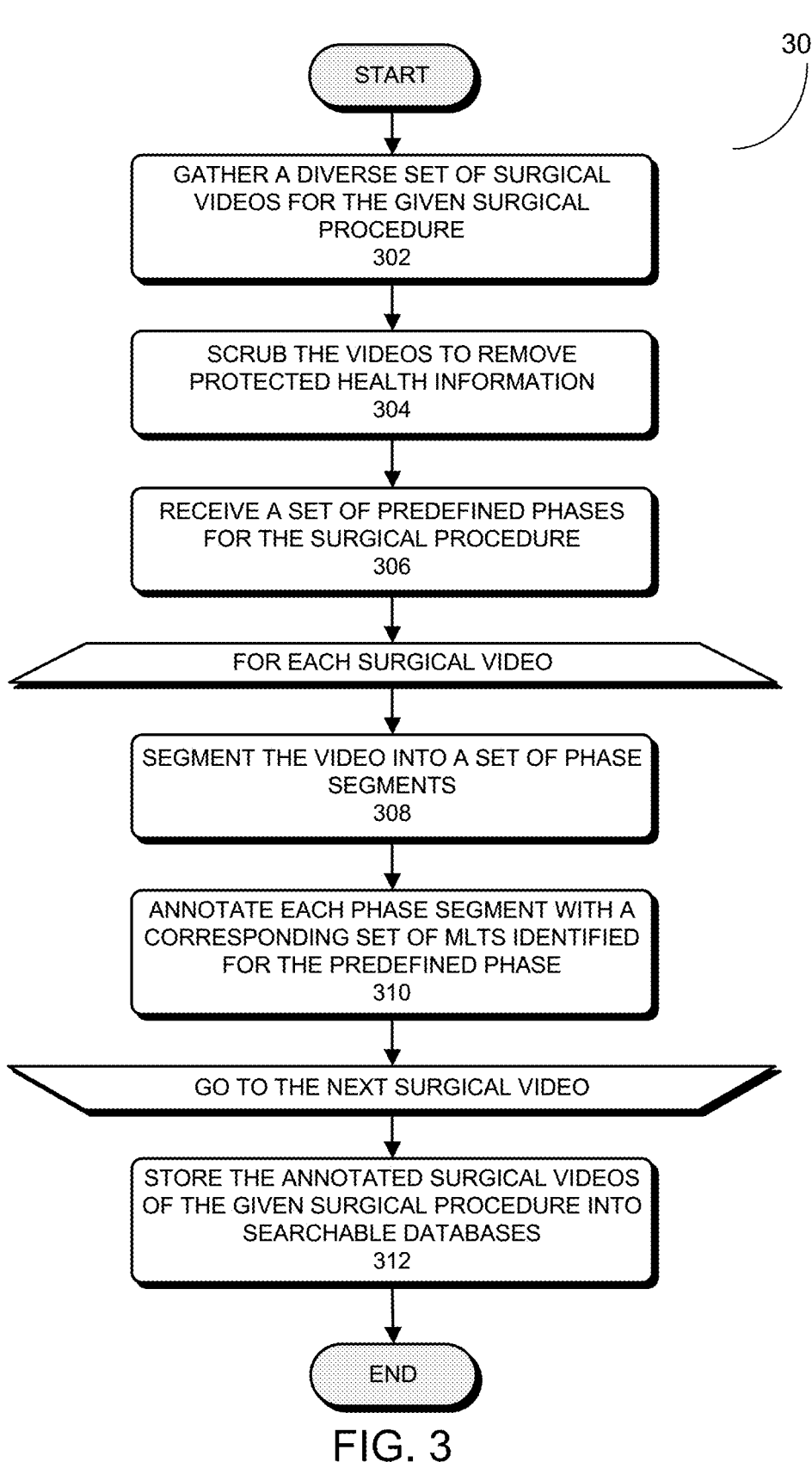
FIG. 3 presents a flowchart illustrating an exemplary process for segmenting and mining surgical videos of a surgical procedure based on a set of predefined phases and identified machine learning targets for the surgical procedure in accordance with some embodiments described herein.

FIG. 3 presents a flowchart illustrating an exemplary process 300 for segmenting and mining surgical videos of a surgical procedure based on a set of predefined phases and identified machine learning targets for the surgical procedure in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique. Process 300 begins by gathering a diverse set of surgical videos for the given surgical procedure (step 302). In some embodiments, the set of surgical videos are collected from a diverse group of doctors and/or hospitals and institutions performing and recording the surgical procedure, and possibly from surgeries performed in different countries. Process 300 then scrubs the gathered videos to remove protected health information (PHI) from the videos to de-identify the video data (step 304). In some embodiments, process 300 can also process the gathered videos to completely anonymize the video data.

Process 300 also receives a set of predefined phases for the surgical procedure (step 306). Some embodiments of identifying the set of predefined phases for the surgical procedure have been described above in conjunction with FIG. 1. Next, based on the set of predefined phases, process 300 segments each surgical video in the set of gathered surgical videos into a set of video segments, wherein each video segment corresponds to a given phase in the set of predefined phases (step 308). In some embodiments, two consecutive phases of the set of predefined phases can be separated by an identifiable "phase boundary" in the surgical videos, which indicates the end of a current phase and the beginning of the next phase in the surgical procedure. For example, the phase boundary can be composed of one or more video images in the surgical video where a particular surgical tool comes into view for the first time during the surgical procedure. Hence, segmenting the surgical videos can involve detecting these phase boundaries in the surgical videos, e.g., by detecting the appearances of certain surgical tools.

Sometimes a given surgical video can be augmented with an audio narrative which explains the actions, events, tools, anatomy, and complications shown in the video images. The audio narratives can be added into the video in real-time when the surgical procedure was being performed, e.g., as a teaching demonstration, or they can be added afterward when the video is being reviewed or described for educational purposes. Moreover, the audio narratives can be transcribed as texts/captions in the relevant video frames. However, in some embodiments, the video can be annotated with texts/captions without accompanying audio narratives. In some embodiments, these text annotations and/or audio narratives within a surgical video can be used to identify phase boundaries and to facilitate segmenting the surgical videos into the predefined phases.

A surgical video of a given surgical procedure typically contains a number of events. Some of the common events include: surgical smoke during electrocautery; bleeding; and adhesions. For example, surgical smoke, together with a hook, a monopolar, a bipolar or a similar cautery tool in view is often a strong indicator for a dissection phase of a surgical procedure. Hence, smoke detection, in combination with tool and anatomy detection, can be used to identify which of the predefined phase of the surgical procedure the video is currently showing, thereby facilitating the surgical video segmentation operation. Other applications of using event detections for surgical video analysis are provided below.

In some embodiments, segmenting a surgical video can include directly identifying the beginning a predefined phase based on the established MLTs for the surgical procedure. More specifically, the MLTs which can be used to identify the beginning of a predefined phase can include the tools, the anatomies, and a combination of the above. For example, in the gastric sleeve procedure, the beginning of the positioning-of-bougie phase (i.e., Phase 5) can be easily identified when a bougie starts appearing in the video frame and starts moving down the stomach in a video frame. In this scenario, the beginning of the positioning-of-bougie phase can be detected based on a tool MLT. As another example, the beginning of the sleeve-pouch-creation phase (i.e., Phase 6) can easily be identified when the stapler is detected in a video frame. In this scenario, the beginning of the sleeve-pouch-creation phase is again detected based on a tool MLT.

Note that segmenting each of the collected surgical videos into the set predefined phases allows for analyzing these surgical videos one phase/stage at a time equipped with an accurate understanding of the content of the processed video segment. In some embodiments, a given predefined phase can be further broken down into a set of subphases, wherein each subphase corresponds to single task among a set of tasks which are performed within the given predefined phase. In such embodiments, it is possible to further divide a phase segment of the surgical video into even smaller segments correspondent to the set of tasks associated with the given phase.

After a surgical video has been segmented, process 300 next annotates each segment of the set of video segments with a corresponding set of MLTs identified for the predefined phase within the surgical procedure (step 310). In some embodiments, annotating video segments involves human annotators using video annotation software to manually label or tag image objects such as tools, anatomies, events, complications shown in the video images of the video segments that match one or more of the corresponding set of MLTs. As shown in FIG. 3, steps 308-310 are repeated for each video in the set of gathered surgical videos.

In some embodiments, steps 308-310 can be performed jointly as a combined annotation operation instead of the two steps in the above-described sequential order. In these embodiments, segmenting a surgical procedure video into the set of predefined phases is treated as one part of the overall annotation operation, wherein the set of predefined phases are machine learning targets/labels for identifying and annotating/labeling the phase segments. Furthermore, within each annotated/labeled phase segment, another part of the overall annotation operation can be performed to identify and label those non-phase MLTs, such as specific tools, anatomies, events, and complications, among others. Hence, in these embodiments, segmenting a surgical procedure video into a set of predefined phases can be considered as a temporal annotation part of the overall annotation operation, and identifying and labeling other MLTs such as tools and anatomies within each phase segment can be considered as a spatial annotation part of the overall annotation operation.

Note that when a given surgical case video has been labeled, the labeled video can be used to assess skills of the surgeon who performed the recorded surgery. Again, denote P; as the predefined phase i within a set of predefined phases for the given surgical procedure P, after labeling the given case video, the labeled MLTs can be expressed as follows:

$T_i$: the set of labeled tools corresponding to phase $P_i$;

$A_i$: the set of labeled anatomies corresponding to phase $P_i$;

$ST_i$: the set of labeled surgical tasks/events corresponding to phase $P_i$;

$C_i$: the union of the set of labeled complications corresponding to $ST_i$, $T_i$, and $P_i$;

$TT_i$: the set of labeled tips and tricks corresponding to phase $P_i$; and $M_i$: the set of all objective and subjective metrics corresponding to $ST_i$, $T_i$, $C_i$, and $P_i$.

Note that $M_i$ can be used to generate a skills score Si for phase $P_i$. Moreover, an overall skills score S for the full procedure of the recorded surgery (and the surgeon who performed the surgery) can be assessed as the union of $M_i$ for all phases of the set of predefined phases:

$$S = \text{Union } \{M_i\} \text{ for all } P_i.$$

After labeling or tagging the gathered videos, process 300 stores the annotated surgical videos of the given surgical procedure into searchable databases for content-based video search and retrieval (step 312). In some embodiments, independent databases are created for each phase of the set of predefined phases by separating annotated video segments belonging to different phases into different databases. In some embodiments, independent databases are created for each MLT in the set of identified MLTs for the given surgical procedure by separating annotated video segments belonging to different MLTs into different databases. Note that, over time, a large searchable database for many different surgical procedures can be constructed in the same manner as segmented and labeled videos. Using these databases, video image data for a desired surgical procedure among the many surgical procedures can be queried based on the various labeled descriptors, such as phases/subphases, anatomies, events, complications, tools, and tips and tricks.

In some embodiments, after establishing machine learning targets for a surgical procedure and processing surgical videos of the surgical procedure based on the identified machine learning targets, a surgical information management system can be constructed for the surgical procedure. In some embodiments, this information management system can be used for the following purposes: (1) segmenting other surgical videos of the surgical procedure; (2) serving as a searchable database of the surgical procedure as reference for future surgeries; and (3) detecting and storing surgical events and unusual anatomies detected from surgical case videos of the surgical procedure.

Note that after establishing the set of predefined phases and machine learning targets for a surgical procedure, the surgical procedure can be specified based on a set of machine learning descriptors. In some embodiments, the set of machine learning descriptors is composed of the set of predefined phases and five categories of the above-described MLTs, i.e., surgical tasks, tools; anatomies; complications; and tips and tricks, but without the metrics MLTs. This is because the metrics MLTs often can not be directed observed within the video images. However, the metrics MLTs can be derived from the other five categories of the MLTs. Note that after a surgical video has been segmented and tagged, the set of machine learning descriptors can be assigned with specific values extracted from the tagged surgical video. Another application of the proposed surgical procedure analysis system is to construct a clinical feedback system based on the above-described set of machine learning descriptors.

Figure 4:
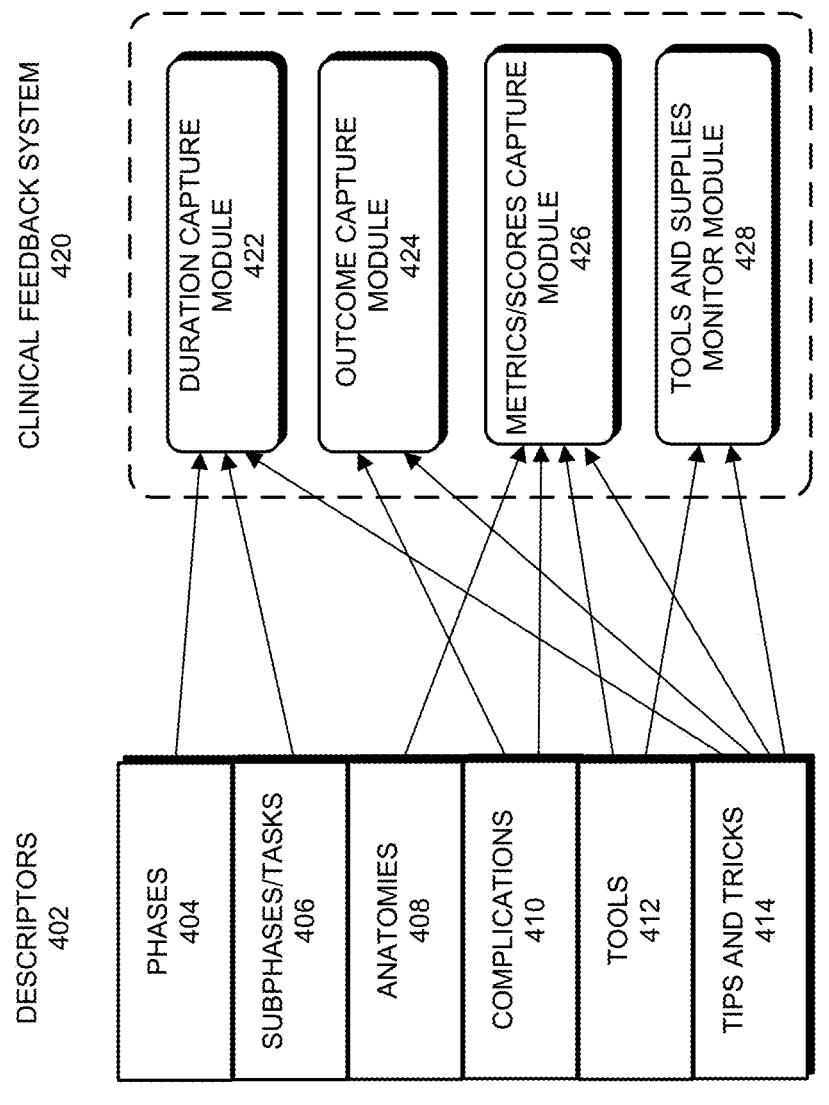
FIG. 4 illustrates an exemplary relationship between a set of machine learning descriptors of a surgical procedure and an exemplary clinical feedback system in accordance with some embodiments described herein.

FIG. 4 illustrates an exemplary relationship between the set of machine learning descriptors 402 of the surgical procedure and an exemplary clinical feedback system 420 in accordance with some embodiments described herein. As can be seen in FIG. 4, the set of machine learning descriptors 402 includes the set of phases 404, the set of subphases/tasks (MLTs) 406, the set of anatomies (MLTs) 408, the set of complications (MLTs) 410, the set of tools (MLTs) 412, and the set of tips and tricks (MLTs) 414. Clinical feedback system 420 includes a duration capture module 422 configured to capture durations of each of the surgical phases 404 and each of the subphases/tasks 406. Clinical feedback system 420 includes an outcome capture module 424 configured to capture the outcomes of the surgical procedure based on the values associated with the set of complications 410. Clinical feedback system 420 also includes a metrics/scores capture module 426 configured to capture the metric values and skills scores of the surgical procedure generated based on the values of the set of complications 410, the set of tools 412, and the set of anatomies 408. Clinical feedback system 420 further includes tools and supplies monitor module 428 configured to determine the surgical tool use information based on the values of the set of tools 412. Note that each of the duration capture module 422, outcome capture module 424, metrics/scores capture module 426, and tools and supplies monitor module 428 can receive or capture the set of tips and tricks (MLTs) 414. Based on the captured or received values by the set of modules 422-428, clinical feedback system 420 can generate a score and/or an overall evaluation for each of the phases 404 and/or tasks 406 of the surgical procedure.

In the above discussion, we mentioned that event detection, such as electrocautery smoke, bleeding, and adhesions can be used as a tool for surgical case video segmentation. Note that these events can be detected either in real-time when surgical case videos are being captured or offline when recorded surgical case videos are reviewed and analyzed. When the event detection is happening in real time, the relevant sections of the live video can be bookmarked even when the surgical procedure is still being recorded.

In addition to the above-described application of video segmentation, surgical event detection can also have the following applications: (1) skills assessment for real cases of the surgical procedure; and (2) outcomes analysis for the real cases of the surgical procedure. More specifically, certain detected events can be used for augmenting/adjusting the skills scores and for outcomes analysis.

For example, if the cautery tool is in view but no smoke is detected for a sustained period of time, it can be an indication of a delay in the procedure due to some unforeseen events. If there is smoke, but the cautery tool cannot be seen, it may be an indication that the tool-tip is off-screen and that the surgeon is accidentally burning some tissue. The detections of the above events can cause the skills score to be adjusted downward. Moreover, the intensity of cautery smoke can be an indicator of the level of carefulness and/or the skill level of the surgeon. In some embodiments, cautery events can be used as tags for content retrieval for dissection steps in any given surgical procedure.

Note that detections of bleeding events during certain phases of a given surgical procedure can be indicators of potential complications. In some embodiments, detections of such events can be used to trigger real-time recommendation of management techniques and/or offering tips/tricks to the surgeon performing the procedure. Moreover, timestamps, locations, and quantities of the bleeding events can be used to make skill assessments. Note that bleeding events can also be used for outcomes analysis. In some embodiments, bleeding events in certain phases of the surgical procedure can be used as tags for video content retrieval and for creating video clips for educational purposes.

Adhesion events, depending on in which phase of the procedure these events are detected and in conjunction with which anatomy, can be used to trigger real-time recommendation of management techniques and/or conversions to open surgery. Note that adhesion events can be used for outcomes analysis. In some embodiments, adhesions events can also be used as tags for video content retrieval.

Note that the disclosed surgical video analysis system can generate a large number of annotated video images for a given surgical procedure. These annotated video data include accurately labeled image objects such as tools, anatomies, tasks, and complications, which themselves become training data for supervised learning problems. Hence, these annotated videos can be used to train machine learning classifiers to automatically detect and identify different MLTs. For example, a machine learning classifier can be built to distinguish and classify different tools involved in the mobilization-of-fundus phase of the gastric sleeve procedure. Another machine learning classifier can be built to distinguish and classify different anatomies involved in the sleeve-pouch-creation phase of the gastric sleeve procedure. A more sophisticated machine learning model can be built to distinguish and classify different tools and anatomies involved in the sleeve-pouch-creation phase of the gastric sleeve procedure. The trained models can then be applied to untagged video segments of the same surgical procedure to perform automatic object detection and tagging. The automatically tagged video segments can be used as additional training data for improving the machine learning model.

FIG. 5 shows a block diagram of an exemplary machine learning system 500 for training machine learning classifiers for automatically tagging surgical videos in accordance with some embodiments described herein. As can be seen in FIG. 5, machine learning system 500 includes a video-gathering subsystem 502, a video cleaning subsystem 504, a temporal-tagging subsystem 506, a spatial-tagging subsystem 508, and a model training subsystem 510 which are coupled in series in the illustrated order.

In the embodiment shown, video-gathering subsystem 502 collects a large set of raw surgical videos 514 of a particular surgical procedure from various sources 512. The diversity of the video sources can be beneficial for the subsequent model training process. In some embodiments, the diversity in the video sources 512 can be measured and controlled by the number of different doctors, the number of different hospital and institutions, and possibly the number of different countries as the resources for the raw surgical videos 514. In some embodiments, video cleaning subsystem 504 is configured to preprocess the raw surgical videos 514 to remove certain portions of a given raw surgical video (e.g., non-intraoperative portions) and also remove PHI information from the given raw surgical video, to generate cleaned surgical videos 516. In some embodiments, temporal-tagging subsystem 506 is configured to receive cleaned surgical videos 516 and a set of phase descriptors specifying a set of predefined surgical phases, and perform phase detection and video segmentation on cleaned surgical videos 516 based on the set of phase descriptors to break down each surgical video into a set of phase segments. Note that temporal-tagging subsystem 506 can perform the aforementioned phase detection and video segmentation on cleaned surgical videos 516 as a fully-manual operation, a fully-automatic operation, or a combined manual and automatic operation. Temporal-tagging subsystem 506 subsequently outputs a set of video segments 518 for each cleaned surgical video 516 corresponding to the set of received phase descriptors. Next, spatial-tagging subsystem 508 is configured to receive the set of video segments 518 for each cleaned surgical video 516 and sets of established machine learning descriptors established for individual video segments 518. Spatial-tagging subsystem 508 is configured to perform tagging/labeling for each video segment 518 of each cleaned surgical video 516 with a set of corresponding established machine learning descriptors, e.g., in a partially automatic manner with the assistance of human annotators, and generate tagged video segments 520 as output.

As shown in FIG. 5, both temporal-tagging subsystem 506 and spatial-tagging subsystem 508 can receive established machine learning descriptors from a surgical video analysis system 530, which itself may or may not be part of machine learning system 500. Some embodiments of surgical video analysis system 530 have been described above in conjunction with FIGS. 1-4. More specifically, from surgical video analysis system 530, temporal-tagging subsystem 506 receives the set of phase descriptors 532 for identifying and tagging/labeling different phase segments in cleaned surgical videos 516, so that each video segment 518 corresponds to a particular surgical phase associated with a given phase descriptor in the set of phase descriptors 532. Furthermore, spatial-tagging subsystem 508 receive sets of machine learning descriptors 534, such as tools, anatomies, events, and complications, for identifying and tagging/labeling various tools, anatomies, events, and complications within different video segments 518, and generate tagged video segments 520.

Next, model training subsystem 510 is configured to receive tagged video segments 520 as input and train various machine learning classifiers based on tagged video segments 520. Note that model training subsystem 510 generates trained machine learning classifiers 522 as output which can include both trained phase classifiers associated with phase descriptors 532 and trained machine learning classifiers associated with machine learning descriptors 534. Trained machine learning classifiers 522 are fed back to both temporal-tagging subsystem 506 and spatial-tagging subsystem 508. In some embodiments, temporal-tagging subsystem 506 can use trained phase classifiers to assist manual or automatic phase detection and labeling of cleaned surgical videos 516 to generate iteratively more accurate phase boundaries for video segments 518. In some embodiments, spatial tagging subsystem 508 can use trained machine learning classifiers 522 to perform automatic object (e.g., surgical tools or anatomies) detection and tagging within video segments 518. These automatically tagged objects can be used as additional training data for model training subsystem 510 to iteratively improve the accuracy of trained machine learning classifiers 522.

Figure 6:
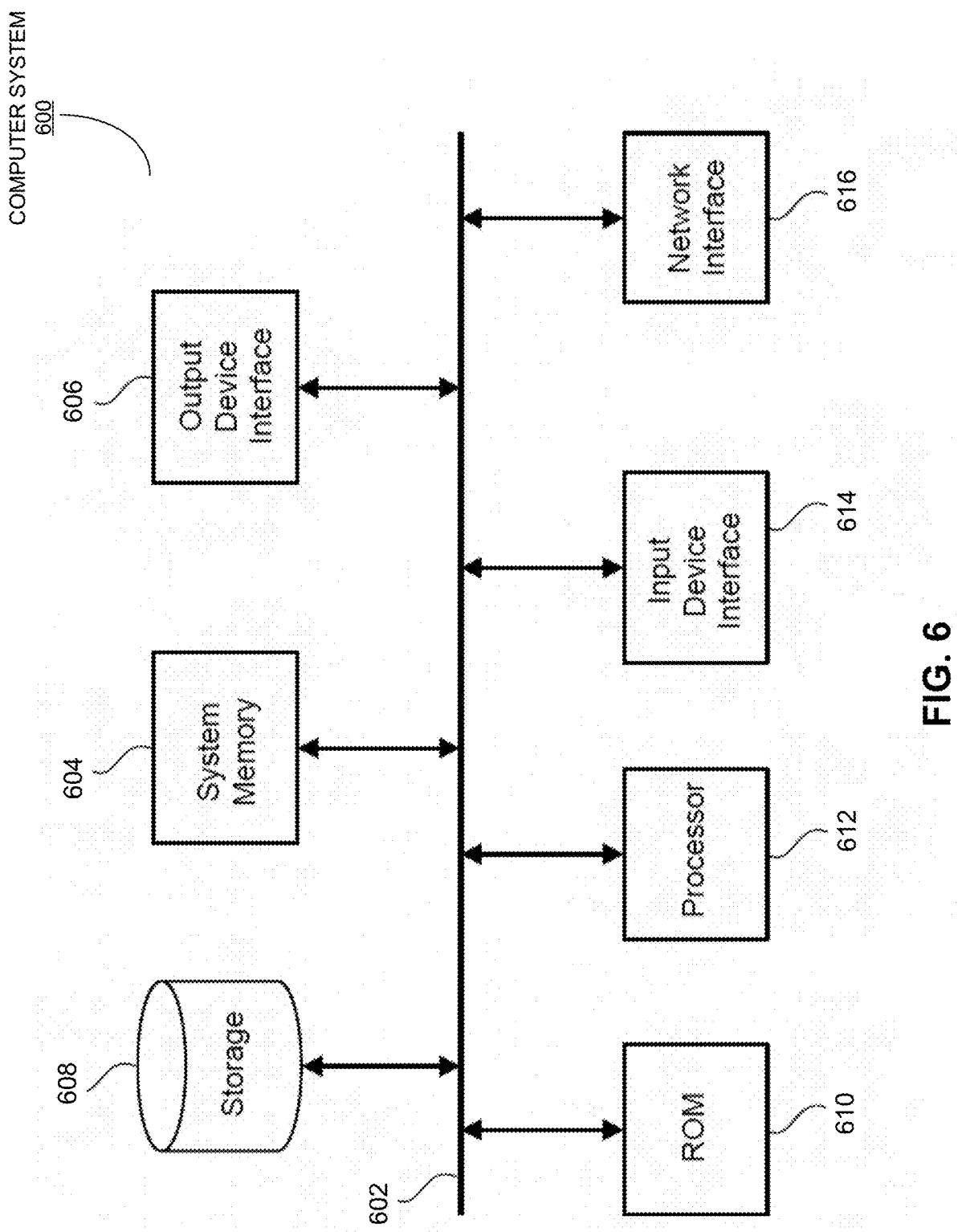
FIG. 6 conceptually illustrates a computer system with which some embodiments of the subject technology can be implemented.

FIG. 6 conceptually illustrates a computer system with which some embodiments of the subject technology can be implemented. Computer system 600 can be a client, a server, a computer, a smartphone, a PDA, a laptop, or a tablet computer with one or more processors embedded therein or coupled thereto, or any other sort of computing device. Such a computer system includes various types of computer readable media and interfaces for various other types of computer readable media. Computer system 600 includes a bus 602, processing unit(s) 612, a system memory 604, a read-only memory (ROM) 610, a permanent storage device 608, an input device interface 614, an output device interface 606, and a network interface 616.

Bus 602 collectively represents all system, peripheral, and chipset buses that communicatively connect the numerous internal devices of computer system 600. For instance, bus 602 communicatively connects processing unit(s) 612 with ROM 610, system memory 604, and permanent storage device 608.

From these various memory units, processing unit(s) 612 retrieves instructions to execute and data to process in order to execute various processes described in this patent disclosure, including the above-described processes of establishing machine learning targets, segmenting and mining surgical videos of different surgical procedures, and training machine learning classifiers for automatically tagging surgical videos in conjunction with FIGS. 1-5. The processing unit(s) 612 can include any type of processor, including, but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 612 can be a single processor or a multi-core processor in different implementations.

ROM 610 stores static data and instructions that are needed by processing unit(s) 612 and other modules of the computer system. Permanent storage device 608, on the other hand, is a read-and-write memory device. This device is a non-volatile memory unit that stores instructions and data even when computer system 600 is off. Some implementations of the subject disclosure use a mass-storage device (such as a magnetic or optical disk and its corresponding disk drive) as permanent storage device 608.

Other implementations use a removable storage device (such as a floppy disk, flash drive, and its corresponding disk drive) as permanent storage device 608. Like permanent storage device 608, system memory 604 is a read-and-write memory device. However, unlike storage device 608, system memory 604 is a volatile read-and-write memory, such a random access memory. System memory 604 stores some of the instructions and data that the processor needs at runtime. In some implementations, various processes described in this patent disclosure, including the processes of establishing machine learning targets, segmenting and mining surgical videos of different surgical procedures, and training machine learning classifiers for automatically tagging surgical videos in conjunction with FIGS. 1-5, are stored in system memory 604, permanent storage device 608, and/or ROM 610. From these various memory units, processing unit(s) 612 retrieves instructions to execute and data to process in order to execute the processes of some implementations.

Bus 602 also connects to input and output device interfaces 614 and 606. Input device interface 614 enables the user to communicate information and select commands to the computer system. Input devices used with input device interface 614 include, for example, alphanumeric keyboards and pointing devices (also called "cursor control devices"). Output device interfaces 606 enables, for example, the display of images generated by the computer system 600. Output devices used with output device interface 606 include, for example, printers and display devices, such as cathode ray tubes (CRT) or liquid crystal displays (LCD). Some implementations include devices such as a touch-screen that functions as both input and output devices.

Finally, as shown in FIG. 6, bus 602 also couples computer system 600 to a network (not shown) through a network interface 616. In this manner, the computer can be a part of a network of computers (such as a local area network ("LAN"), a wide area network ("WAN"), or an Intranet, or a network of networks, such as the Internet. Any or all components of computer system 600 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A computer-implemented method, the method comprising:

receiving a surgical video of a surgical procedure performed by a surgeon as a plurality of video images;

identifying, in a plurality of subsets of video images of the plurality of video images, a surgical task, a surgical tool, and an anatomy;

for each subset of video images, creating a metric that establishes an associative relationship among at least two of the surgical task, the surgical tool, or the anatomy within the subset of video images, and annotating the subset of video images based on the metric, the surgical task, the surgical tool, or the anatomy;

computing an evaluation score for the surgeon according to an overall metric that comprises a union of all metrics from the plurality of subsets of video images; and training a machine learning (ML) classifier using each annotated subset of video images to detect similar surgical tasks, surgical tools, anatomies, or metrics in other surgical videos.

2. The computer-implemented method of claim 1, wherein annotating comprises adding text or captions that describe the metric, the surgical task, the surgical tool, or the anatomy in the subset of video images based on 1) user input, 2) output of an annotation operation that is responsive to input based on the metric, the surgical task, the surgical tool, or the anatomy, or 3) a combination thereof.

3. The computer-implemented method of claim 1 further comprising segmenting the surgical video into a plurality of phase segments corresponding to a set of predefined phases of the surgical procedure, wherein each phase segment comprises a different subset of video images of the plurality of video images and corresponds to a predefined phase of the set of predefined phases that is associated with the metric, the surgical task, the surgical tool, or the anatomy.

4. The computer-implemented method of claim 1 further comprising producing a cleaned surgical video by identifying protected health information or non-intraoperative portions within one or more video images of the surgical video and removing the one or more video images from the surgical video.

5. The computer-implemented method of claim 4, wherein identifying comprises performing automatic object detection upon the cleaned surgical video.

6. The computer-implemented method of claim 1, wherein the ML classifier is a first ML classifier, wherein the method further comprises using the annotated subset of video images to train a second ML classifier to detect similar subsets of video images in other surgical videos.

7. The computer-implemented method of claim 1, wherein identifying comprises:

receiving a set of one or more ML descriptors; and using the ML classifier to detect the surgical task, the surgical tool, or the anatomy within the subset of video images that match the set of one or more ML descriptors.

8. A system comprising:

at least one processor; and memory having stored instructions which when executed by the at least one processor causes the system to:

receive a surgical video of a surgical procedure performed by a surgeon as a plurality of video images;

identify, in a plurality of subsets of video images of the plurality of video images, a surgical task, a surgical tool, and an anatomy;

for each subset of video images, creating a metric that establishes an associative relationship among at least two of the surgical task, the surgical tool, or the anatomy within the subset of video images, and annotate the subset of video images based on the metric, the surgical task, the surgical tool, or the anatomy;

computing an evaluation score for the surgeon according to an overall metric that comprises a union of all metrics from the plurality of subsets of video images; and train a machine learning (ML) classifier using each annotated subset of video images to detect similar surgical tasks, surgical tools, anatomies, or metrics in other surgical videos.

9. The system of claim 8, wherein the instructions to annotate comprises instructions to add text or captions that describe the metric, the surgical task, the surgical tool, or the anatomy in the subset of video images based on 1) user input, 2) output of an annotation operation that is responsive to input based on the metric, the surgical task, the surgical tool, or the anatomy, or 3) a combination thereof.

10. The system of claim 8, wherein the memory comprises further instructions to segment the surgical video into a plurality of phase segments corresponding to a set of predefined phases of the surgical procedure, wherein each phase segment is comprises a different subset of video images of the plurality of video images and corresponds to a predefined phase of the set of predefined phases that is associated with the metric, the surgical task, the surgical tool, or the anatomy.

11. The system of claim 8, wherein the memory has further instructions to produce a cleaned surgical video by identifying protected health information or non-intraoperative portions within one or more video images of the surgical video and removing the one or more video images from the surgical video.

12. The system of claim 11, wherein the instructions to identify comprises instructions to perform automatic object detection upon the cleaned surgical video.

13. The system of claim 8, wherein the ML classifier is a first ML classifier, wherein the memory comprises further instructions to use the annotated subset of video images to train a second ML classifier to detect similar subsets of video images in other surgical videos.

14. The system of claim 8, wherein instructions to identify comprises instructions to:

receive a set of one or more ML descriptors; and use the ML classifier to detect the surgical task, the surgical tool, or the anatomy within the subset of video images that match the set of one or more ML descriptors.

15. A non-transitory machine-readable medium comprising instructions which when executed by at least one processor of a system, causes the system to:

receive a surgical video of a surgical procedure performed by a surgeon as a plurality of video images;

identify, in a plurality of subsets of video images of the plurality of video images, a surgical task, a surgical tool, and an anatomy;

for each subset of video images, creating a metric that establishes an associative relationship among at least two of the surgical task, the surgical tool, or the anatomy within the subset of video images, and annotate the subset of video images based on the metric, the surgical task, the surgical tool, or the anatomy;

compute an evaluation score for the surgeon according to an overall metric that comprises a union of all metrics from the plurality of subsets of video images; and train a machine learning (ML) classifier each annotated subset of video images to detect similar surgical tasks, surgical tools, anatomies, or metrics in other surgical videos.

16. The non-transitory machine-readable medium of claim 15, wherein the instructions to annotate comprises instructions to add text or captions that describe the metric, the surgical task, the surgical tool, or the anatomy in the subset of video images based on 1) user input, 2) output of an annotation operation that is responsive to input based on the metric, the surgical task, the surgical tool, or the anatomy, or 3) a combination thereof.

17. The non-transitory machine-readable medium of claim 15 comprises further instructions to segment the surgical video into a plurality of phase segments corresponding to a set of predefined phases of the surgical procedure, wherein each phase segment comprises a different subset of video images of the plurality of video images and corresponds to a predefined phase of the set of predefined phases that is associated with the metric, the surgical task, the surgical tool, or the anatomy.

18. The non-transitory machine-readable medium of claim 15 comprises further instructions to produce a cleaned surgical video by identifying protected health information or non-intraoperative portions within one or more video images of the surgical video and removing the one or more video images from the surgical video.

19. The non-transitory machine-readable medium of claim 18, wherein the instructions to identify comprises instructions to perform automatic object detection upon the cleaned surgical video.

20. The non-transitory machine-readable medium of claim 15, wherein the ML classifier is a first ML classifier, wherein the non-transitory machine-readable medium comprises further instructions to use the annotated subset of video images to train a second ML classifier to detect similar subsets of video images in other surgical videos.

* * * * *